United States Patent [19]

Martines

[11] 4,101,572

[45] Jul. 18, 1978

[54] USE OF PHOSPHORUS DERIVATIVES AS STABILIZING AGENTS FOR PERCHLOROMETHYL MERCAPTAN

[75] Inventor: Vincent C. Martines, White Plains, N.Y.

[73] Assignee: Stauffer Chemical Company, Westport, Conn.

[21] Appl. No.: 753,121

[22] Filed: Dec. 22, 1976

[51] Int. Cl.$^2$ .................................... C07C 148/04
[52] U.S. Cl. ............................................. 260/543 H
[58] Field of Search ................................. 260/543 H

[56] References Cited

U.S. PATENT DOCUMENTS

| | | | |
|---|---|---|---|
| 2,545,285 | 3/1951 | Kamlet | 260/543 H |
| 2,575,290 | 11/1951 | Ohsol et al. | 260/543 H |
| 2,647,143 | 7/1953 | Pitt et al. | 260/543 H |
| 2,666,081 | 1/1954 | Churchill | 260/543 H |
| 2,759,969 | 8/1956 | Jonas | 260/543 H |
| 3,014,071 | 12/1961 | Hoyt et al. | 260/543 H |
| 3,673,246 | 6/1972 | Meyer et al. | 260/543 H |
| 3,808,270 | 4/1974 | Rupp et al. | 260/543 H |
| 3,878,243 | 4/1975 | Zupancic | 260/543 H |
| 3,968,155 | 7/1976 | Guerin | 260/543 H |
| 3,993,693 | 11/1976 | Bhutani | 260/543 H |

FOREIGN PATENT DOCUMENTS

| | | | |
|---|---|---|---|
| 508,163 | 12/1954 | Canada | 260/543 H |
| 1,437,908 | 3/1966 | France | 260/543 H |

OTHER PUBLICATIONS

Sosnovsky "Chem Reviews", vol. 58, pp. 509–512 (1958).

*Primary Examiner*—Norman Morgenstern
*Attorney, Agent, or Firm*—Roger S. Benjamin

[57] ABSTRACT

A method for stabilizing perchloromethyl mercaptan by including therein effective amounts of phosphorus derivatives.

7 Claims, No Drawings

USE OF PHOSPHORUS DERIVATIVES AS STABILIZING AGENTS FOR PERCHLOROMETHYL MERCAPTAN

BACKGROUND OF THE INVENTION

This invention relates to improvements in the stabilization of perchloromethyl mercaptan. More particularly, it relates to the use of phosphorus derivatives as stabilizing agents.

Perchloromethyl mercaptan, $Cl_3CSCl$, also known as trichloromethanesulfenyl chloride, has commercial importance as an intermediate in the manufacture of fungicides, bactericides, germicides, herbicides, soil fumigants and pharmaceuticals.

Perchloromethyl mercaptan was first described in a production scheme by Rathke in Annalen, Volume 167, at page 195 (1873). Rathke's method, which is still in use today, utilizes an iodine catalyst. The reaction scheme operates most efficiently at temperatures below about 40° C., in accordance with the following equations:

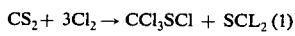

$$CS_2 + 3Cl_2 \rightarrow CCl_3SCl + SCl_2 \quad (1)$$

$$2CS_2 + 5Cl_2 \rightarrow 2CCl_3SCl + S_2Cl_2 \quad (2)$$

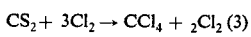

$$CS_2 + 3Cl_2 \rightarrow CCl_4 + {}_2Cl_2 \quad (3)$$

In addition to sulfur dichloride, sulfur chloride (also known as sulfur monochloride) and carbon tetrachloride, the reaction can also form thiophosgene and other compounds as unwanted byproducts. Although more volatile byproducts such as carbon tetrachloride and sulfur dichloride can be removed from the reaction mixture by distillation, it is extremely difficult to separate perchloromethyl mercaptan from sulfur chloride by this method. This is due to the fact that the boiling points of perchloromethyl mercaptan and sulfur chloride are very close to each other.

The prior art has proposed several methods for improving the basic Rathke method. For example, U.S. Pat. No. 3,544,625 to Masat, discloses a method for producing perchloromethyl mercaptan by chlorinating carbon disulfide in the presence of a solution of inorganic acids, such as hydrochloric acid. U.S. Pat. No. 3,673,246 to Meyer et al, discloses a continuous process for producing perchloromethyl mercaptan wherein carbon disulfide is reacted with chlorine on or in intimate contact with activated carbon at temperatures of about −5° C. to +100° C. U.S. Pat. No. 3,808,270 to Rupp et al discloses a continuous process for producing perchloromethyl mercaptan by reacting carbon disulfide and chlorine in a reaction zone filled with granular active carbon completely immersed in the liquid reaction mixture while maintaining temperatures in the range of about 40° C. to about 135° C. U.S. Pat. No. 3,878,243 to Zupancic discloses a homogeneous catalyst system comprising a lead salt of a carboxylic acid which is soluble in carbon disulfide. Notwithstanding, the proliferation of technology dealing with approaches other than the iodine catalyzed method, the basic Rathke method is still the predominant approach used to produce perchloromethyl mercaptan in the United States and abroad.

In the production of perchloromethyl mercaptan via the iodine catalyzed method, the crude perchloromethyl mercaptan must be separated from the reaction byproducts and the iodine catalyst by distillation. Since perchloromethyl mercaptan produced by the iodine catalyzed method is accomplished in a batch operation, some lapse of time occurs before the crude perchloromethyl mercaptan can be purified by distillation. One problem that occurs, is that the crude perchloromethyl mercaptan and its byproducts will react in the following manner:

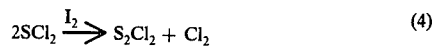

$$2SCl_2 \xrightarrow{I_2} S_2Cl_2 + Cl_2 \quad (4)$$

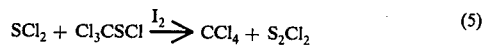

$$SCl_2 + Cl_3CSCl \xrightarrow{I_2} CCl_4 + S_2Cl_2 \quad (5)$$

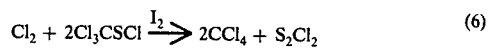

$$Cl_2 + 2Cl_3CSCl \xrightarrow{I_2} 2CCl_4 + S_2Cl_2 \quad (6)$$

The above reactions are undesirable because they produce $S_2Cl_2$, a byproduct which is difficult to separate from perchloromethyl mercaptan by distillation, thereby reducing the purity of the final product. Also, the $Cl_2$ produced in reaction (4) can react with perchloromethyl mercaptan as in reaction (6) to further reduce the yield of perchloromethyl mercaptan. Reactions (5) and (6) can also convert perchloromethyl mercaptan to $CCl_4$, further reducing the yield of perchloromethyl mercaptan.

U.S. Pat. No. 3,479,253 discloses stabilizers for the production of sulfur dichloride such as trialkyl phosphites, phosphorus pentachloride or trialkyl phosphates, to be used in the distillation of sulfur dichloride to inhibit the decomposition of sulfur dichloride into sulfur monochloride and chlorine.

The present invention has achieved improvements in the production of perchloromethyl mercaptan via the use of phosphorus derivatives as stabilizers which are believed to suppress the occurrence of the undesirable reactions occurring in equations 4, 5 and 6.

DESCRIPTION OF THE PREFERRED EMBODIMENT

In accordance with the present invention, the degradation of crude perchloromethyl mercaptan has been effectively prevented by the addition of small amounts of phosphorus derivatives to the crude perchloromethyl mercaptan. In essence, the undesirable byproducts of reactions 4, 5 and 6 have been suppressed.

The phosphorus derivatives that have been found to be most effective in accomplishing the purposes of the present invention are phosphonates having the following structural formula:

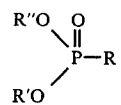

wherein R independently is hydrogen, hydrocarbyl or substituted hydrocarbyl; R' and R" independently are R or chlorine, however, R, R' and R" cannot all be hydrogen simultaneously.

Typical examples of hydrocarbyl groups are alkyl, cycloalkyl, aralkyl, alkaryl, and aryl, with the alkyl groups having from 1 to about 20 carbon atoms, and preferably from 1 to about 10 carbon atoms. The alkyl groups can be straight, branch chained or cyclic.

Typical examples of substituted alkyl and substituted aryl as used herein are meant to designate alkyl or aryl groups having attached thereto at least one substituent of the type: halogen, cyano, carboxyl, carboxylate, amido, amino, nitro, hydroxy or alkoxy, with the proviso that the substituents not adversely affect the preparation of perchloromethyl mercaptan. The preferred substituents are halogen, and most preferably, chlorine.

A typical aryl group can be phenyl and the like. Alkaryl groups can be cresyl, xylyl and the like. Aralkyl can be benzyl and the like.

Typical examples of the preferred phosphonates found to be especially effective in stabilizing the crude perchloromethyl mercaptan have alkyl and substituted alkyl groups containing from about 1 to about 10 carbon atoms.

The addition of the phosphonate stabilizers is accomplished most effectively by adding it to the crude perchloromethyl mercaptan immediately after the iodine catalyzed batch reaction is completed, or if in the carbon catalyzed continuous process, by contacting directly with the carbon disulfide prior to reaction.

It should be noted that the reaction temperatures required for batch process production of PMM are generally lower than the temperatures which can be maintained in a continuous process. For example, batch process temperatures generally vary from about 10° C. to about 40° C., when using a carbon or iodine catalyst. This is due to the fact that higher temperatures favor formation of carbon tetrachloride in the batch process, whereas in the continuous carbon catalyzed process, the temperatures can exist above 130° C. without adverse effects, when operated in accordance with U.S. Pat. No. 3,808,270.

The phosphonate stabilizers are generally added in amounts which vary from about 0.5 to about 5%, and preferably from about 1 to about 3% by weight of the crude perchloromethyl mercaptan product. Larger amounts can be used, however, no advantage is accrued thereby. In general, it has been found that use of the phosphonate stabilizers in the stated manner significantly reduces the formation of undesirable byproducts occurring in reactions (4), (5) and (6), thereby improving the purity and the yield of perchloromethyl mercaptan.

In the example which follows, all parts and percentages are by weight unless otherwise specified.

EXAMPLE

Crude perchloromethyl mercaptan was produced in a batch reactor via the iodine catalyzed route as described by Rathke. Upon completion of the reaction, five samples, of the crude perchloromethyl mercaptan each weighing about 4 grams were withdrawn from the reactor. One sample, designated as the "control" was immediately contacted with about 2 drops (approximately 0.05 grams) of dimethyl methylphosphonate (DMMP) and the sample was then analyzed by gas chromatograhy. It was found necessary to stabilize the control prior to analysis by gas chromatography due to the fact that the crude perchloromethyl mercaptan samples can react in accordance with equations 4, 5 and 6, when experiencing the elevated temperatures in the gas chromagrahic analyzer, thereby leading to an inaccurate analysis. Thus, contacting the control sample with the stabilizing agent enabled an accurate analysis of the crude PMM drawn from the reactor.

The remaining samples were treated in the following manner:

Sample 2 — was immediately contacted with DMMP. This sample was then retained at room temperature for four hours, then analyzed by gas chromatography.

Sample 3 — was retained for four hours at room temperature, then contacted with DMMP, and the sample analyzed by gas chromatography.

Sample 4 — was contacted immediately with DMMP, and then held for 2 hours at room temperature, and for 2 hours at 0° C., and then analyzed by gas chromatography.

Sample 5 — was retained for 2 hours at room temperature, then for 2 hours at 0° C., then contacted with DMMP and analyzed by gas chromatography.

The results are tabulated below:

| Component | CRUDE PMM SAMPLES | | | | |
|---|---|---|---|---|---|
| | 1 (Control) | 2 | 3 | 4 | 5 |
| $Cl_2$ | 0.10 | 0.71 | 0.16 | 0.53 | 0.07 |
| $CS_2$ | 7.07 | 7.09 | 5.49 | 6.85 | 5.30 |
| $SCl_2$ | 41.65 | 40.73 | 37.20 | 41.45 | 40.21 |
| $CCl_4$ | 5.67 | 5.78 | 8.27 | 5.71 | 8.06 |
| $S_2Cl_2$ | 1.32 | 1.15 | 2.75 | 1.08 | 1.79 |
| $Cl_3CSCl$ | 43.91 | 44.24 | 45.92 | 44.13 | 44.57 |
| Total | 99.72 | 99.70 | 99.79 | 99.75 | 100.00 |
| % $CS_2$ Conversion | 74.6 | 74.7 | 80.6 | 75.3 | 80.7 |
| % $CS_2$ Conversion to PMM | 64.5 | 64.5 | 66.2 | 65.1 | 66.2 |
| % $CS_2$ Conversion to $CCl_4$ | 10.1 | 10.2 | 14.4 | 10.2 | 14.5 |
| % Selectivity for PMM | 86.5 | 86.3 | 82.1 | 86.5 | 82.0 |
| % Selectivity for $CCl_4$ | 13.5 | 13.7 | 17.9 | 13.5 | 18.0 |
| Ratio PMM/$S_2Cl_2$ | 33.3 | 38.5 | 16.7 | 42.8 | 24.9 |

As can be seen from the data, the untreated samples, that is those samples which were left unstabilized for a number of hours before being analyzed, showed a substantial increase in $S_2Cl_2$ and $CCl_4$ over both the control and samples 2 and 4, which were immediately stabilized with DMMP.

What is claimed is:

1. A method of stabilizing crude perchloromethyl mercaptan produced by the iodine catalyzed chlorination of carbon disulfide which comprises adding an amount of dimethyl methylphosphonate effective to stabilize said crude perchloromethyl mercaptan.

2. The method of claim 1 wherein said dimethyl methylphosphonate is added in amounts from about 0.5% to about 5% by weight of the crude perchloromethyl mercaptan.

3. The method of claim 1 wherein said chlorination is batch.

4. The method of claim 1 wherein said chlorination is continuous.

5. The method of claim 2 wherein said amounts vary from about 1 to about 3% by weight of the perchloromethyl mercaptan produced.

6. A stabilized perchloromethyl mercaptan composition consisting essentially of: (1) crude perchloromethyl mercaptan produced by the iodine catalyzed chlorination of carbon disulfide, and (2) an amount of dimethyl methylphosphonate effective to stabilize said crude perchloromethyl mercaptan.

7. The composition of claim 6 wherein the dimethyl methylphosphonate is present in an amount of from about 0.5% to about 5% by weight of the crude perchloromethyl mercaptan.

* * * * *

UNITED STATES PATENT AND TRADEMARK OFFICE
CERTIFICATE OF CORRECTION

PATENT NO. : 4,101,572
DATED : July 18, 1978
INVENTOR(S) : Vincent C. Martines

It is certified that error appears in the above-identified patent and that said Letters Patent are hereby corrected as shown below:

Column 1, Line 27, delete "$_2Cl_2(3)$" and substitute -- $S_2Cl_2(3)$ --.

Signed and Sealed this

Eighth Day of May 1979

[SEAL]

Attest:

RUTH C. MASON
Attesting Officer

DONALD W. BANNER
Commissioner of Patents and Trademarks